United States Patent
Sambusseti

(10) Patent No.: US 10,350,051 B2
(45) Date of Patent: Jul. 16, 2019

(54) ORTHOTOPIC ARTIFICIAL BLADDER ENDOPROSTHESIS

(71) Applicant: Antonio Sambusseti, Cremona (IT)

(72) Inventor: Antonio Sambusseti, Cremona (IT)

(*) Notice: Subject to any disclaimer, the term of this patent is extended or adjusted under 35 U.S.C. 154(b) by 0 days.

(21) Appl. No.: 15/514,696

(22) PCT Filed: Sep. 28, 2015

(86) PCT No.: PCT/IB2015/057427
§ 371 (c)(1),
(2) Date: Mar. 27, 2017

(87) PCT Pub. No.: WO2016/051333
PCT Pub. Date: Apr. 7, 2016

(65) Prior Publication Data
US 2017/0231748 A1    Aug. 17, 2017

(30) Foreign Application Priority Data
Sep. 30, 2014  (IT) .............................. MI2014A1707

(51) Int. Cl.
*A61F 2/04* (2013.01)

(52) U.S. Cl.
CPC ...... *A61F 2/042* (2013.01); *A61F 2210/0004* (2013.01); *A61F 2210/0009* (2013.01); *A61F 2210/0014* (2013.01); *A61F 2220/0008* (2013.01); *A61F 2230/0071* (2013.01); *A61F 2250/001* (2013.01); *A61F 2250/0008* (2013.01); *A61F 2250/0059* (2013.01)

(58) Field of Classification Search
CPC ...................................................... A61F 2/042
See application file for complete search history.

(56) References Cited

U.S. PATENT DOCUMENTS

| | | | |
|---|---|---|---|
| 4,219,026 A | 8/1980 | Layton | |
| 4,655,745 A * | 4/1987 | Corbett | A61M 25/02 604/103.07 |
| 5,518,498 A * | 5/1996 | Lindenberg | A61F 2/94 128/DIG. 25 |

(Continued)

FOREIGN PATENT DOCUMENTS

| | | | | |
|---|---|---|---|---|
| CA | 2802556 A1 * | 12/2011 | ........ | A61M 25/0017 |
| DE | 102010024820 A1 | 12/2011 | | |

(Continued)

OTHER PUBLICATIONS

University of Colorado Hospital. "The Orthotopic Neobladder". pp. 1-8. Oct. 2006.*

(Continued)

*Primary Examiner* — Andrew M Iwamaye
(74) *Attorney, Agent, or Firm* — Vorys, Sater, Seymour and Pease LLP

(57) ABSTRACT

An orthotopic artificial bladder endoprosthesis includes a casing made of a PGA fiber fabric; the casing having two first connectors for the connection with the ureters of a patient and a second connector for the connection with the urethra of a patient; a support element being inserted in the casing; the support element being switchable between an extended configuration, in which it supports and maintains in position the casing, and a retracted configuration.

14 Claims, 2 Drawing Sheets

(56) References Cited

U.S. PATENT DOCUMENTS

| | | | |
|---|---|---|---|
| 6,048,330 A | 4/2000 | Atala | |
| 6,296,668 B1 | 10/2001 | Desgrandchamps et al. | |
| 6,682,473 B1 | 1/2004 | Matsuura et al. | |
| 6,855,126 B2 * | 2/2005 | Flinchbaugh | A61F 5/4405 604/106 |
| 2004/0243104 A1 * | 12/2004 | Seddon | A61M 25/0017 604/540 |
| 2005/0065468 A1 * | 3/2005 | Goebel | A61L 29/049 604/96.01 |
| 2005/0124978 A1 * | 6/2005 | Kim | A61M 25/0017 604/544 |
| 2006/0229553 A1 * | 10/2006 | Hammack | A61M 25/04 604/96.01 |
| 2007/0219488 A1 | 9/2007 | Francescatti | |
| 2007/0276507 A1 | 11/2007 | Bertram et al. | |
| 2008/0097467 A1 | 4/2008 | Gruber et al. | |
| 2009/0118829 A1 * | 5/2009 | Powell | A61F 2/12 623/8 |
| 2010/0010478 A1 * | 1/2010 | Nissenkorn | A61L 29/06 604/544 |
| 2010/0324540 A1 * | 12/2010 | Paulen | A61M 25/0017 604/544 |
| 2011/0196197 A1 * | 8/2011 | Forsell | A61B 17/0469 600/37 |
| 2011/0276081 A1 * | 11/2011 | Kilemnik | A61B 17/320725 606/198 |
| 2012/0232652 A1 * | 9/2012 | Mora | A61F 2/12 623/8 |
| 2013/0158522 A1 | 6/2013 | Lisowsky et al. | |
| 2014/0214175 A1 * | 7/2014 | Barron | A61F 2/04 623/23.66 |
| 2015/0223924 A1 | 8/2015 | Sambusseti et al. | |
| 2015/0223953 A1 * | 8/2015 | Pendleton | A61F 2/852 623/23.68 |
| 2017/0216012 A1 | 8/2017 | Sambusseti | |

FOREIGN PATENT DOCUMENTS

| | | | |
|---|---|---|---|
| FR | 2116838 A5 * | 7/1972 | A61F 2/042 |
| FR | 2759575 A1 | 8/1998 | |
| WO | 9850100 A1 | 11/1998 | |
| WO | 0178576 A2 | 10/2001 | |
| WO | 2007075545 A2 | 7/2007 | |
| WO | 2007095193 A2 | 8/2007 | |
| WO | 2008048764 A1 | 4/2008 | |
| WO | WO 2011160875 A1 * | 12/2011 | A61F 2/042 |
| WO | 2012120326 A1 | 9/2012 | |
| WO | 2014057444 A1 | 4/2014 | |
| WO | 2014060911 A1 | 4/2014 | |
| WO | 2015159185 A1 | 10/2015 | |
| WO | 2016051330 A1 | 4/2016 | |

OTHER PUBLICATIONS

International Search Report and Written Opinion dated Jan. 14, 2016 for PCT/IB2015/057427 to Antonio Ambusseti filed Sep. 28, 2015.

Machine Translation for FR2116838 A5, published Jul. 21, 1972, Applicant: Sowinski Kazimierz Maria.

* cited by examiner

ORTHOTOPIC ARTIFICIAL BLADDER ENDOPROSTHESIS

CROSS-REFERENCE TO RELATED APPLICATIONS

This is a § 371 National Stage Application of International Application No. PCT/IB2015/057427 filed on Sep. 28, 2015, claiming the priority of Italian Patent Application No. MI2014A001707 filed on Sep. 30, 2014.

FIELD OF THE INVENTION

The present invention refers to an orthotopic artificial bladder endoprosthesis.

The application of the present invention lies in the replacement of the bladder of a patient, if the latter is suffering from incurable diseases serious as to compromise the correct function thereof.

BACKGROUND OF THE INVENTION

Known bladder endoprostheses comprise a casing made of biocompatible and biodegradable material. The casing defines, at its interior, an enclosure for containing urine.

By way of example, the casing is made of PGA fiber fabric.

In order to give the casing the necessary structural rigidity, the known endoprosthesis comprises structural elements applied externally on the casing itself.

By way of example, the structural elements comprise a plurality of arms connected to each other to define an asterisk configuration and shaped so as to have dome-like form.

The structural elements are made of rigid biocompatible and biodegradable material. By way of example, the structural elements are made of PGA/PLA copolymer.

The casing is sufficiently rigid so as to stably keep its shape and flexible such that it can be manually compressed to ensure that it empties.

The casing has a connection element located at a lower portion of the casing to connect with the patient's urethra. Similarly, two connection bodies are located at the top to enable connection with the ureters.

The connection element and bodies are also obtained with the biodegradable material.

Following the implant of the endoprosthesis in the patient, there is the formation of a musculo-fibrous tissue layer or fibrous capsule (not impermeable) around the casing, while the latter decomposes. In such a manner, a neobladder is generated around the endoprosthesis.

During the resorption, there is the formation of a transition epithelium layer, which is also called urothelium, which is advantageously impermeable. This is essential for ensuring the correct functioning of the prosthesis and of the neobladder that is being formed.

The obtainment of this type of endoprosthesis is complex and costly.

Indeed, the casing made of biocompatible and biodegradable material must be carefully coupled to the structural elements, which must in turn be precisely made and carefully shaped.

This renders the obtainment complex, long and costly. Examples of bladder endoprosthesis showing the above mentioned drawbacks are hereafter illustrated.

A known orthotopic artificial bladder endoprosthesis is disclosed in WO2014/057444 as comprising a cuff substantially rigid and shaped as a balloon and having an internal surface and an external surface defining a compartment for the containment of the urine.

Another known orthotopic artificial bladder endoprosthesis is disclosed in FR2759575 as comprising a containment element of a double layer material having an internal layer and an external layer of different materials, said materials having the double function of allowing the placing of the containment element on the patient body without rejection problems and without being damaged by the urine storing up in said containment element and, at the same time, said layers are aimed to keep the shape of the containment element itself.

Another known document, defined by WO2007/095193, discloses a bladder prosthesis defined by two hemispherical being connected one to the other and provided of external flange suitable for handling said portion before or during the surgical operation and for allowing the coupling between said two portions.

Other known technical solutions, as the one disclosed in WO2008/048764, refers to devices for performing gynecologic and urologic procedures that comprise a scaffold or frame apt to be inserted, for example, in the uteri chamber so as to distend said chamber in a way corresponding to the distention of the uteri chamber in case of liquid use and with said structure which also comprises a containment element having the uterus shape and fixed to a shaft sliding with respect to a sheat together with the containment element, said containment element that, when projecting out from the sheat, distends or expands in a radial direction so as to distend the uterus walls and allowing, in such a way, the performing of procedures such as tissue removal and similar.

Another known solution is disclosed in WO2014/060911 and refers to a orthotopic artificial bladder endoprosthesis comprising two equivalent portions having a substantially semi-spherical shape and coupled together by means of resorbable suture and a frame or scaffold externally fixed to each of said two portions with the function of allowing said two portions to maintain a dome-like form even under the weight of the growing fibrous tissue.

Other known solutions for artificial bladder endoprosthesis are disclosed, for example, in WO2012/120326 which refers to an artificial bladder internally provided with a mechanical shaft apt to drive a valve for the opening/closing of the urethra.

SUMMARY OF THE INVENTION

In this context, the technical task underlying the present invention is to propose an orthotopic artificial bladder endoprosthesis which overcomes the abovementioned drawbacks of the prior art.

In particular, the object of the present invention is to provide an orthotopic artificial bladder endoprosthesis that is simpler and quicker to make.

The specified technical task and the specified object are substantially achieved by an orthotopic artificial bladder endoprosthesis comprising the technical characteristics set forth in one or more of the enclosed claims.

BRIEF DESCRIPTION OF THE DRAWINGS

Further characteristics and advantages of the present invention will be clearer from the exemplifying and therefore non-limiting description of a preferred but not exclusive embodiment an orthotopic artificial bladder endoprosthesis, as illustrated in the enclosed drawings, in which.

DETAILED DESCRIPTION OF THE PREFERRED EMBODIMENTS

Figure 1:
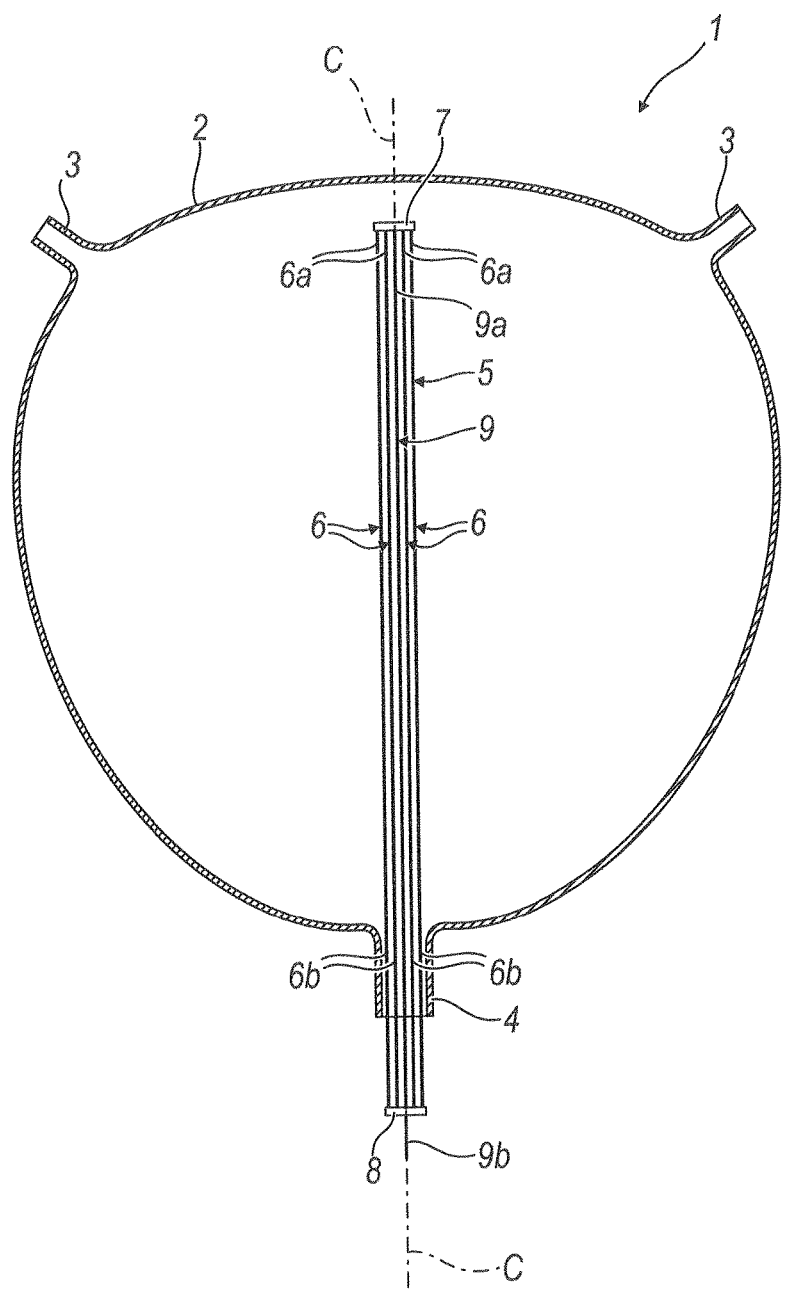
FIG. 1 is a schematic view of an orthotopic artificial bladder endoprosthesis in accordance with the present invention in a first configuration.
Figure 2:
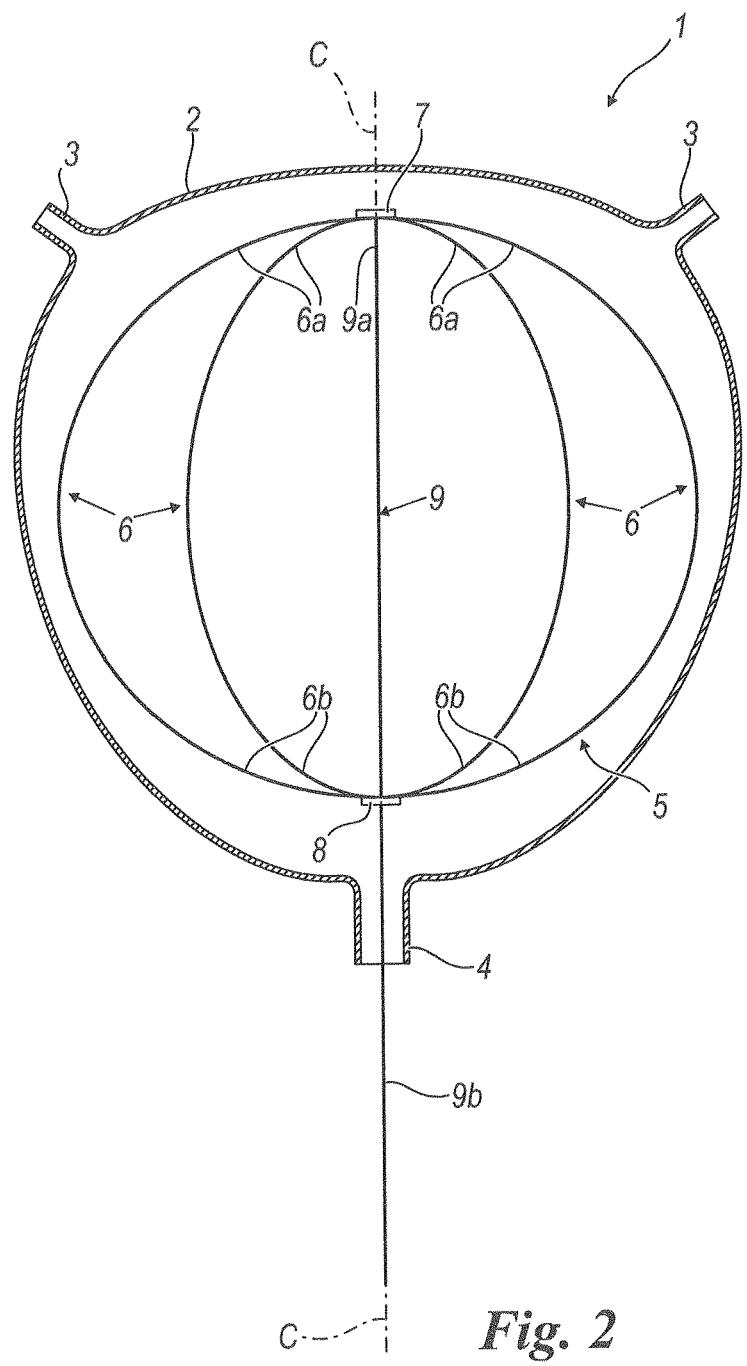
FIG. 2 is a schematic view of the endoprosthesis of FIG. 1 in a second configuration.

With reference to the enclosed drawings, reference number 1 overall indicates an orthotopic artificial bladder endoprosthesis in accordance with the present invention.

The endoprosthesis 1 comprises a casing 2 made with a PGA fiber fabric.

The PGA (polyglycolide or polyglycolic acid) used in the fabric—with which the casing 2 is obtained—is preferably homopolymer. PGA is a highly biocompatible and resorbable polymer that is resistant to urine. In detail, the resorption time of PGA is approximately one month.

The fabric casing 2 can be obtained by weaving the PGA thread in various ways, giving rise to a knitted fabric, a woven fabric or a non-woven fabric.

Preferably, the fabric of the casing 2 is a knitted fabric, still more preferably a warp knitted fabric. In such cases, the fabric of the casing 2 has a rougher surface capable of assuming a net configuration with sufficiently small meshes.

In detail, its weft is such that its interstitial space is less than 200 µm, preferably around 160 µm, corresponding to an average area of the holes equal to approximately 0.02 mm$^2$. This ensures impermeability to urine, preventing leaks.

Furthermore, once the endoprosthesis 1 is inserted, the covering is impregnated with blood and in particular with plasma, which allows the antibiotic drugs to be effective.

Furthermore, the fabric of the casing 2 is preferably textured so as to give it even greater surface roughness and greater rigidity and impermeability. The greater roughness of the fabric limits the risk of adhesion of the fibrous capsule.

Purely by way of example, the fabric of the casing 2 has a thickness substantially comprised between 0.3 mm and 0.6 mm, more preferably comprised between 0.4 mm and 0.53 mm, still more preferably being substantially 0.45 mm.

In addition, the thread with which the fabric of the casing is obtained has a density comprised between 50 and 200 denier.

The casing 2 substantially has a spherical shape and has first connectors 3 intended to be connected, by means of resorbable suture, with the ureters of a patient.

The casing 2 also has a second connector 4 intended to be connected, by means of resorbable suture, to the urethra of a patient.

The casing 2 can be obtained by means of joining two hemispherical caps. Alternatively, the casing 2 can be obtained in a single piece.

Purely by way of example, the casing 2 has a volume comprised between 300 cm$^3$ and 400 cm$^3$, preferably substantially equal to 350 cm$^3$.

The endoprosthesis 1 also comprises a support element 5 inserted within the casing 2.

The support element 5 is deformable in a manner such to be switchable between an extended configuration and a retracted configuration.

In the extended configuration, the support element 5 is marked by a maximum volume. Consequently, the support element 5 enlarges the casing 3 from the interior, supporting it and maintaining it in position. In this configuration, the casing 2 maintains the desired and appropriate shape during the step of creation of the neobladder and of simultaneous dissolution of the casing 2 itself.

In the retracted configuration, the support element 5 has minimum volume and is unable to enlarge and support the casing 2. This configuration is usefully employed in the step of storage and installation of the endoprosthesis 1 and in the step of elimination of the support element 5 when the neobladder is formed.

The support element 5 comprises a plurality of arms 6 that are connected to each other.

In detail, each arm 5 has a first end 6a and a second end 6b. The first ends 6a are connected to each other, as are the second ends 6b.

The arms 6 are arranged parallel to each other and around a central axis "C", angularly equidistant in a manner such that the support element 5 has an axially-symmetric configuration.

The arms 6 all have the same length.

In accordance with the present invention, when the support element 5 is situated in the retracted configuration, the distance between the first 6a and the second ends 6b is maximum. When the support element 5 is situated in the extended configuration, the distance between the first 6a and the second ends 6b is minimum.

In more detail, when the support element 5 is situated in the retracted configuration, the arms 6 have a substantially rectilinear form. When the support element 5 is situated in the extended configuration, the arms 6 are deformed in order to have a substantially curved form with a mutual moving-apart progression.

In such a manner, the deformed and curved arms 6 support the casing 2, which maintains a desired form.

The support element 5 comprises a first connection body 7, to which the first ends 6a of the arms 6 are fixed.

The first connection body 7 can be shaped as a circle or ring. The first ends 6a of the arms 6 are fixed at the perimeter of the first connection body 7, at points preferably equidistant from each other.

Furthermore, the support element 5 also comprises a second connection body 8 to which the second ends 6b of the arms 6 are connected and fixed.

The second connection body 8 can be shaped as a circle or ring. The second ends 6b of the arms 6 are fixed at the perimeter of the second connection body 8, at points preferably equidistant from each other.

In the passage between the retracted configuration and the extended configuration, the first 7 and the second 8 connection body are in a mutual approaching and/or moving-apart relationship.

In order to allow the deformation of the support element 5 from the retracted configuration to the extended configuration (and vice versa), the support element 5 comprises a rod 9 having a first 9a and a second end 9b.

The rod 9 is fixed to the first connection body 7 at its first end 9a. The second end 9b is free.

The rod 9 is arranged parallel to the arms 6.

The rod 9 is preferably centrally arranged with respect to the arms 6. In particular, the rod 9 is placed along the central axis "C".

The rod 9 passes through an opening made in the second connection body 8, continuing beyond.

In other words, the length of the rod 9 is greater than the length of the arms 6.

During use, the rod 9 is necessary in order to move the first ends 6a of the arms 6 close to the second ends 6b. Indeed, by maintaining the second connection body 8 in pulling the rod 9, the first connection body 7 is moved close to the second connection body 8. Similarly, by maintaining the rod 9 stopped and pushing the second connection body 8, the first 7 and the second 8 connection body approach each other.

The approaching of the first 7 and second 8 connection body causes an action of compression on the arms 6, which are bent, opening them wide. The extended configuration is thus obtained.

Advantageously, the support element 5 is made of nickel-titanium intermetallic compound, also known by the term 'nitinol'.

Nitinol is a shape memory alloy provided with a very high elasticity (a characteristic known with the term 'superelasticity'); it is not magnetic and it has optimal corrosion resistance and good ductility. In addition, it has good biocompatibility.

Preferably, both the arms 6 and the first 7 and the second 8 connection body are made of nitinol.

The arms 6 are covered with a layer of turbostratic pyrolytic carbon.

The layer of turbostratic pyrolytic carbon has a thickness comprised between 0.2 μm and 0.3 μm.

The application of the carbon layer on the arms 6 allows avoiding the risk that the fibrous capsule being formed could adhere to the support element 5. In addition, the layer of turbostratic pyrolytic carbon prevents the formation of crusts due to urine.

Also the first 7 and the second 8 connection body can be covered with a layer of turbostratic pyrolytic carbon.

Advantageously, the entire support element 5 is covered with a layer of turbostratic pyrolytic carbon.

The endoprosthesis 1 also comprises a constraining member (not illustrated in the enclosed figures) operatively placed between the second connection body 8 and the rod 9. The constraining member allows stably fixing the relative position between the second connection body 8 and the rod 9. In particular, the constraining member is active for maintaining the support element 5 in the extended configuration, i.e. when the first 7 and the second 8 connection body are at their minimum distance.

In addition, a urine drain tube (not illustrated) can be provided, which is inserted in the urethra of the patient. The drain tube is optional.

The end of the drain tube inserted in the urethra of the patient reaches a point just downstream of the sphincter with respect to the endoprosthesis 1.

The end of the drain tube comprises a Dacron® mesh in order to achieve the connection with the urethra.

The drain tube is made of silicone and is (internally and/or externally) covered with a layer of turbostratic pyrolytic carbon in order to prevent crusts.

The drain tube has minimum length of 15 cm.

The drain tube has a substantially circular section. The internal diameter is approximately 6 mm while the external diameter is approximately 9 mm.

During use, the endoprosthesis 1 in accordance with the present invention is implanted once the natural bladder of the patient, e.g. compromised by a serious disease, is removed.

Once the connections with the ureters have been obtained, by means of resorbable sutures, the support element 5 is brought into the extended configuration. In order to do this, the surgeon moves the first connection body 7 and the second connection body 8 close to each other, by simultaneously operating on the rod 9 and on the second connection body 8.

The second connector 4 is fixed to the urethra by means of a resorbable suture and the operation site is reclosed.

At this point, it is necessary to wait the pre-established time period in order to allow the reconstruction of the neobladder.

After said period has passed, the surgeon reopens the operation site and moves the support element 5 back into the retracted configuration, e.g. by means of endoscope through the patient's urethra. Its function has now terminated, since the neobladder has been successfully formed.

In order to extract the support element 5, the surgeon operates by means of endoscope, removing such element through the urethra, preventing further surgical operations.

The invention thus described attains the preset object.

Indeed, the use of the support element, and its introduction in the PGA casing during manufacture of the endoprosthesis, allows a considerable simplification of the attainment of the endoprosthesis itself.

Indeed, the casing made of resorbable fabric and the deformable support element are obtained independent of each other and particular expedients and precision are not required.

A further and non-negligible advantage lies in the fact that the moving-apart of the support element can occur without any need of a further, invasive cystostomy, sparing the patient further discomfort and hospital stay.

The invention claimed is:

1. An orthotopic artificial bladder endoprosthesis for insertion into a patient, comprising:
    a casing made of PGA fiber fabric, the casing having two first connectors for connection with ureters of the patient, respectively, and a second connector for connection with a urethra of the patient, the casing having an interior diameter and a spherical shape; and
    a support element inserted in the casing, the support element being deformable to change from an extended configuration, in which the support element has a maximum outer diameter that spans at least a majority of the interior diameter of the casing such that the support element supports and enlarges the casing from within the interior of the casing to maintain the shape of the casing, to a retracted configuration and vice versa, the support element comprising a plurality of arms, each having a first end and a second end, the arms being constrained to each other at the first end and the second end;
    wherein the endoprosthesis is adapted and configured such that after the endoprosthesis is inserted into the patient, the support element is then changed from the retracted configuration to the extended configuration, wherein the support element has a longitudinal axis and in the extended configuration the portion of each said arm between the respective arm first end and second end moves transversely outwardly away from the longitudinal axis lateral to the longitudinal axis, and
    wherein the endoprosthesis is adapted and configured such that the extended support element maintains the casing enlarged during dissolution of the casing within the patient,
    wherein, in the retracted configuration, the arms have a rectilinear form and, in the extended configuration, the arms are curved according to a mutual moving-apart expansion, wherein in the extended position each arm has an entirely convex outer profile.

2. The endoprosthesis according to claim 1, wherein the arms are arranged parallel to each other and around a central axis and are angularly equidistant in a manner such that the support element has an axially-symmetric configuration.

3. The endoprosthesis according to claim 1, wherein, in the retracted configuration, the distance between the first and the second ends of the arms is maximum and, in the extended configuration, the distance between the first and the second ends of the arms is minimum.

4. The endoprosthesis according to claim 1, wherein the support element is made of nickel-titanium intermetallic compound.

5. The endoprosthesis according to claim 1, further comprising a first connection body to which the first ends of the arms are fixed, and a second connection body to which the second ends of the arms are fixed; the first connection body and the second connection body being movable in a mutual approaching and/or moving-apart relationship to pass between the retracted configuration and the extended configuration.

6. The endoprosthesis according to claim 5, further comprising a rod having a first end fixed to the first connection body and a free second end, said rod passing through or in proximity to said second connection body, and the second connection body is an end of the support element.

7. The endoprosthesis according to claim 6, comprising a constraining member active between the rod and the second connection body, the constraining member configured to fix the rod with respect to the second connection body in the extended configuration of the support element.

8. The endoprosthesis according to claim 6, wherein, in the retracted configuration, the distance between the first and the second ends of the arms is maximum and, in the extended configuration, the distance between the first and the second ends of the arms is minimum, and wherein the second connection body is an end of the support element.

9. The endoprosthesis according to claim 1, wherein each arm is covered with a layer of turbostratic pyrolytic carbon.

10. The endoprosthesis according to claim 1, comprising a first connection body to which the first ends of the arms are fixed, and a second connection body to which the second ends of the arms are fixed; the first and the second connection body being movable in a mutual approaching and/or moving-apart relationship to pass between the retracted configuration and the extended configuration, wherein the arms are exposed to directly contact the interior wall of the casing when the support element is in the extended configuration, wherein the arms are spaced from each other in the extended configuration to extend radially from the first connection body and the second connection body as longitudinal curved arms having the entirely convex outer profile from the first connection body to the second connection body.

11. The endoprosthesis according to claim 1, wherein the support element is changed from the retracted configuration to the extended configuration by moving the ends of the arms together, and wherein the support element is changed from the extended configuration to the retracted configuration by moving the ends of the arms apart.

12. An orthotopic artificial bladder endoprosthesis for insertion into a patient, comprising:
a casing made of PGA fiber fabric, the casing having two first connectors for connection with the ureters of the patient, respectively, and a second connector for connection with the urethra of the patient, the casing having an interior diameter and a spherical shape; and
a support element inserted in the casing, the support element being deformable to change from an extended configuration, in which the support element has a maximum outer diameter that spans at least a majority of the interior diameter of the casing such that the support element supports and enlarges the casing from within the interior of the casing to maintain the shape of the casing, to a retracted configuration and vice versa, the support element comprising a plurality of arms, each having a first end and a second end, the arms being constrained to each other at the first end and the second end,
wherein, in the retracted configuration, the arms have a rectilinear form and, in the extended configuration, the arms are curved according to a mutual moving-apart expansion, wherein in the extended configuration each arm has an entirely convex outer profile.

13. The endoprosthesis according to claim 12, wherein the support element is changed from the retracted configuration to the extended configuration by moving the ends of the arms together, and wherein the support element is changed from the extended configuration to the retracted configuration by moving the ends of the arms apart,
wherein, in the retracted configuration, the distance between the first and the second ends of the arms is maximum and, in the extended configuration, the distance between the first and the second ends of the arms is minimum,
further comprising a first connection body to which the first ends of the arms are fixed, and a second connection body to which the second ends of the arms are fixed; the first connection body and the second connection body being movable in a mutual approaching and/or moving-apart relationship to pass between the retracted configuration and the extended configuration,
further comprising a rod having a first end fixed to the first connection body and a free second end, said rod passing through or in proximity to said second connection body, and the second connection body is an end of the support element.

14. The endoprosthesis according to claim 13, wherein the arms are exposed to directly contact the interior wall of the casing when the support element is in the extended configuration, wherein the arms are spaced from each other in the extended configuration to extend radially from the first connection body and the second connection body as longitudinal curved arms having the entirely convex outer profile from the first connection body to the second connection body.

* * * * *